(12) United States Patent
Hu

(10) Patent No.: US 10,053,416 B1
(45) Date of Patent: Aug. 21, 2018

(54) PROCESS FOR PRODUCING LONG CHAIN AMINO ACIDS AND DIBASIC ACIDS

(71) Applicant: VITAWORKS IP, LLC, North Brunswick, NJ (US)

(72) Inventor: Songzhou Hu, Princeton, NJ (US)

(73) Assignee: VITAWORKS IP, LLC, North Brunswick, NJ (US)

( * ) Notice: Subject to any disclaimer, the term of this patent is extended or adjusted under 35 U.S.C. 154(b) by 0 days.

(21) Appl. No.: 15/647,966

(22) Filed: Jul. 12, 2017

(51) Int. Cl.
C07C 227/00 (2006.01)
C07C 227/18 (2006.01)
C07C 231/24 (2006.01)

(52) U.S. Cl.
CPC .......... *C07C 227/18* (2013.01); *C07C 231/24* (2013.01)

(58) Field of Classification Search
CPC ..... C07C 227/04; C07C 51/06; C07C 231/10; C07C 249/08
USPC ....................................... 554/114
See application file for complete search history.

(56) References Cited

U.S. PATENT DOCUMENTS

2011/0251414 A1* 10/2011 Pees .................. C07C 227/08
554/114

FOREIGN PATENT DOCUMENTS

| CN | 102089272 A | * | 6/2011 | ........... C07C 51/353 |
| CN | 103804209 A | * | 5/2014 | |
| WO | 2017088218 A1 | | 6/2017 | |

* cited by examiner

*Primary Examiner* — Deborah D Carr
(74) *Attorney, Agent, or Firm* — Myers Wolin, LLC

(57) ABSTRACT

There is disclosed a process for the separation of long chain amino acid and long chain dibasic acid, comprising: (1) mixing the mixed amide derivatives with an aqueous solution of ammonia or ammonium hydroxide in the presence or absence of solvent or catalyst; (2) subjecting the solution or suspension of step (1) to an hydrolysis reaction; and (3) recovering excess ammonia and solvent in the presence of solvent in step (1) by evaporation to provide a mixture of long chain amino acid and alkylamine or ammonium salts of long chain dibasic acid and alkanoic acid.

21 Claims, 4 Drawing Sheets

PROCESS FOR PRODUCING LONG CHAIN AMINO ACIDS AND DIBASIC ACIDS

TECHNICAL FIELD

The present invention relates to a process for the production and separation of long chain amino acids, dibasic acids, short chain alkylamines, and alkanoic acids.

BACKGROUNDS OF THE INVENTION

Long chain saturated aliphatic amino acids, lactams, and dibasic acids are important monomers for long chain nylons and engineering plastics. Nylons are a class of polymers that contain amide bond on their backbone of chains. Nylons are one of the most widely used, most numerous in types, and most consumed class of engineering plastics.

Because of their unusual molecular structure, long chain nylons possess extraordinary physical properties, i.e., higher mechanical strength than metal, low hygroscopicity, excellent resistance to oil, low temperature, abrasion, and chemical corrosion, and most importantly, easy to fabricate. Long chain nylons are made into many kinds of plastics products, spun to fibers, and stretched to thin films. Long chain nylons are also used in paints and hot melt adhesives. Hence, long chain nylons find wide applications in automobile, electrical, electronic, telecommunications, petrochemical, and aerospace industries.

Long chain amino acids and lactams are used industrially as monomers to produce nylon-9, nylon-11, and nylon-12.

Long chain dibasic acids are condensed with diamines industrially as starting materials to produce nylon-610, nylon-612, nylon-510, nylon-512, nylon-1010, and nylon-1212.

WO 2017/088218, the co-pending U.S. Ser. No. 15/601,556, and U.S. Ser. No. 15/644,708, all of which by the present inventor, disclose a novel process for the coproduction of long chain amino acids and dibasic acids from keto fatty acid derivatives. According to these prior art, long chain keto fatty acid derivatives are reacted with hydroxylamine to form an oxime derivative, which is subjected to the Beckmann rearrangement to yield a mixture of two amide derivatives. These amide derivatives are hydrolyzed with an acid or a basic agent to a mixture of products containing long chain amino acids and dibasic acids, which are isolated by a process of step-wise neutralization. The hydrolysis is carried out with an alkali hydroxide as the hydrolysis with an acid is extremely slow and takes excessively long time to complete.

Copending application U.S. Ser. No. 15/635,874 discloses a process for the complete separation of each component from a mixture of the hydrolysis products in the production of long chain dibasic acids and amino acids without discharging any waste aqueous stream.

The process according to WO 2017/088218 and U.S. Ser. No. 15/635,874 makes use of an alkali hydroxide, most preferably sodium hydroxide, and an acid, most preferably sulfuric acid, to accomplish the production and separation. As a result, a large amount of sodium sulfate is generated in the production process. As a byproduct, sodium sulfate is costly to form from sodium hydroxide and sulfuric acid. In addition, sodium sulfate is of little value and is increasingly difficult to dispose of.

It is an object of the present invention to disclose a process for the production of long chain amino acids and dibasic acids by performing the hydrolysis of mixed amide derivatives with ammonia or ammonium hydroxide.

It is another object of the present invention to disclose a process for the separation of each component from a mixture of the products by the ammonium hydroxide hydrolysis. According to the process of the present invention, long chain amino acids and dibasic acids are produced and separated simply, efficiently, and economically with high yields and excellent purity. The only byproduct is ammonium sulfate, which is a valuable commodity as a fertilizer.

DESCRIPTION OF THE INVENTION

Figure 1:
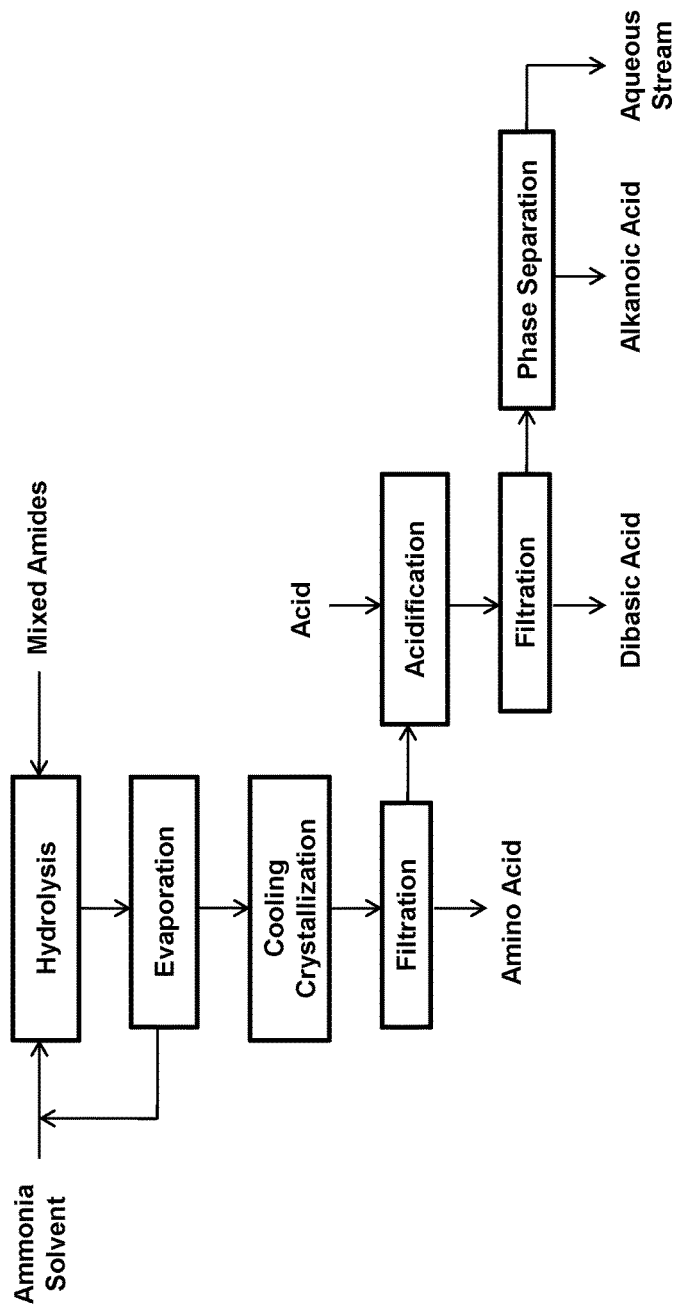
FIG. 1. Schematic flowchart for the production and separation of long chain amino acid, dibasic acid, alkylamine, and alkanoic acid from their mixture in the case of an ammonium hydroxide hydrolysis.

The main objective of the present invention is to disclose a process for carrying out the hydrolysis of the mixed amide derivatives of the following structures:

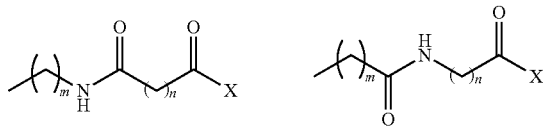

from the Beckmann rearrangement of oxime fatty acid derivatives with ammonia or ammonium hydroxide to yield a mixture of main products of the following structures:

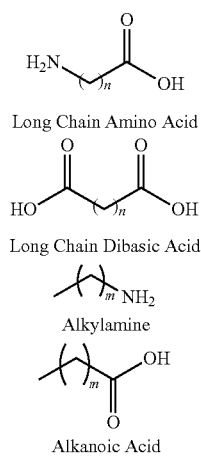

Long Chain Amino Acid

Long Chain Dibasic Acid

Alkylamine

Alkanoic Acid wherein m is an integer from 0 to 10, n is an integer from 6 to 20; X is OR or $NR_1R_2$, wherein OR is OH, $C_1$-$C_8$ monohydric alcohol or $C_1$-$C_8$ polyhydric alcohol, and $R_1$ and $R_2$ are each independently hydrogen or $C_1$-$C_8$ alkyl group.

When m=5, n=10, the main products are 11-aminoundecanoic acid, dodecanedioic acid, hexylamine, and heptanoic acid. Because the starting material of commercial grade is obtained from castor oil, significant amount of stearic acid is also present as an impurity in the mixture of products.

When m=7, n=8, the main products are 9-aminononanoic acid, sebacic acid, octylamine, and pelargonic acid.

When m=5, n=12, the main products are 13-aminotridecanoic acid, tetradecanedioic acid (brassylic acid), hexylamine, and heptanoic acid.

The present inventor has found that the mixed amide derivatives from the Beckmann rearrangement can be hydrolyzed with an aqueous solution of ammonia or ammonium hydroxide. The hydrolysis reaction is carried out at elevated temperature from 100° C. to 280° C., preferably from 150 to 250° C., more preferably from 160 to 240° C., most preferably from 180° C. to 220° C. The pressure for the hydrolysis reaction is from autogenous to 260 bars.

The hydrolysis reaction can be carried out in the atmosphere of air or under the protection of inert gas, i.e., helium, argon, or nitrogen.

The molar ratio of ammonia to the mixed amide derivative can be varied from 1 to 20, preferably from 2 to 10, more preferably from 3 to 8, most preferably from 4 to 8.

The hydrolysis of the mixed amide derivative can also be performed in the presence of a catalyst. Useful catalyst is found in the group consisting of alkali and ammonium salts of hydroxide, bicarbonate, carbonate, bisulfite, sulfite, sulfate, nitrate, phosphate, and a mixture of two or more thereof. Preferably, the catalyst is selected from alkali hydroxides, most preferably, the catalyst is sodium hydroxide. The catalyst is added in an amount of 0.01% to 10%, more preferably from 0.1% to 5%, most preferably 0.5% to 2%, by weight of the mixed amide derivatives. The alkali metals are lithium, sodium, potassium, or cesium.

An aqueous solution of organic solvent can be used in the hydrolysis reaction to help dissolve the mixed amide derivatives, which is beneficial to accelerate the hydrolysis. A useful solvent is selected from the group consisting of methanol, ethanol, isopropanol, propanol, tetrahydrofuran, dioxane, tert-butanol, isobutanol, butanol, and a mixture of two or more thereof. The solvent is preferably selected from alcohols, more preferably methanol or ethanol, most preferably the same alcohol as in the mixed amide ester. The content for the selected solvent in an aqueous mixture is varied from 5% to 95%, more preferably in the range from 30 to 70%, most preferably from 40% to 60%.

The hydrolysis reaction can be carried out continuously, semi-continuously, or batch wise. After the hydrolysis, excess ammonia and the solvent in an aqueous solvent are removed by evaporation to provide a solution or suspension of long chain amino acid and a mixture of alkylamine or ammonium salts of long chain dibasic acid and alkanoic acid. It is important to point out that alkylamine is not evaporated or evaporated insignificantly during the process of ammonia removal. Alkylamine is found to form a salt with long chain dibasic acid or alkanoic acid. After removal of excess ammonia, the strongly alkaline solution or suspension becomes neutral, and the long chain amino acid is precipitated.

Figure 4:
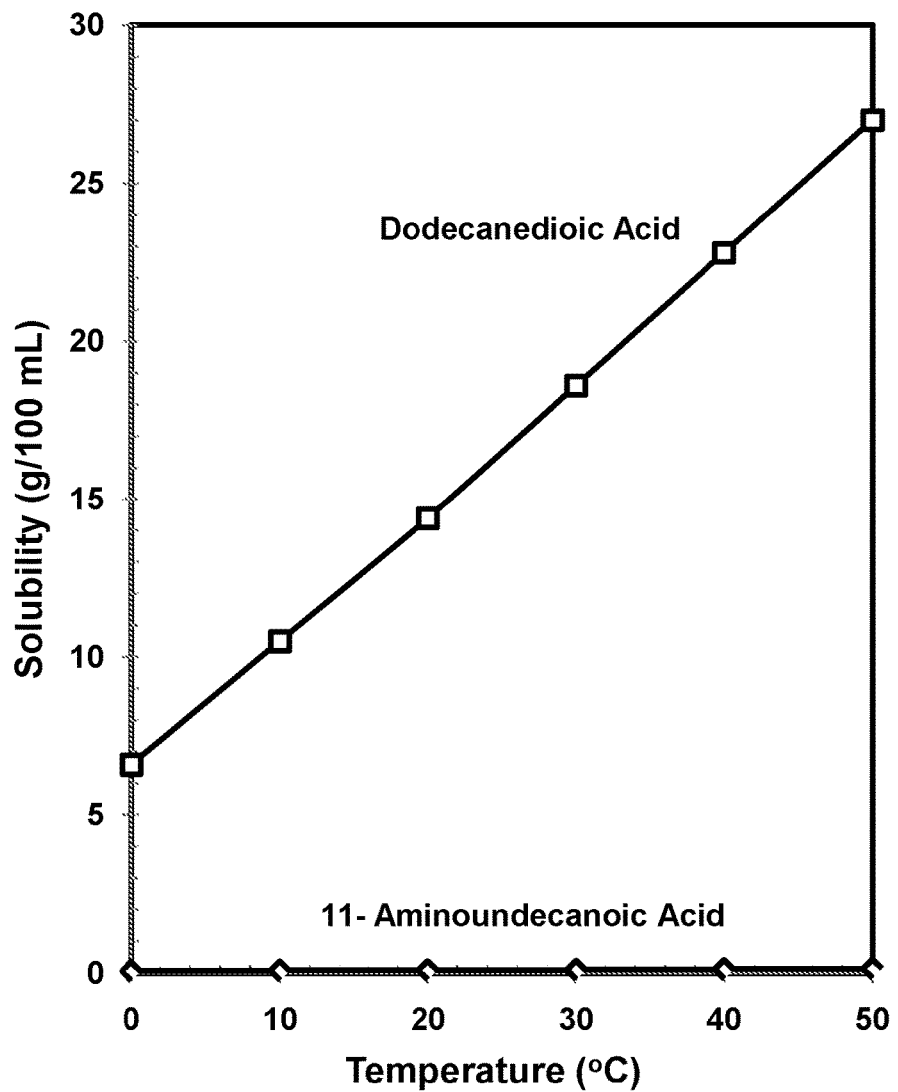
FIG. 4. Solubility curve of 11-aminoundecanoic acid and dodecanedioic acid in 5% aqueous solution of ammonium hydroxide.

In one embodiment of the present invention, schematically illustrated in FIG. 1, the solution or suspension is further cooled to crystallize the long chain amino acid, which can be recovered by means of solid-liquid separation to provide a mother liquor containing the ammonium or alkylamine salts of long chain dibasic acid and alkanoic acid. FIG. 4 demonstrated a large difference in solubility of the ammonium salt of dodecanedioic acid and 11-aminoundecanoic acid. It becomes apparent that the ammonium salt of dodecanedioic acid is soluble and becomes more soluble as temperature increases, while 11-aminoundecanoic acid is nearly insoluble in 5% solution of ammonium hydroxide. The three components in the mother liquor, i.e., alkylamine, dodecanedioic acid, and alkanoic acid, can be separated according to one of the following three methods.

According to the first method for separating each component in the mother liquor, the solution is acidified to precipitate long chain dibasic acid and to generate alkanoic acid as an oil. The long chain dibasic acid is recovered by means of solid-liquid separation to provide a mother liquor, from which the alkanoic acid is separated by a phase separation to provide a solution, to which a basic agent is added in the presence of an extractant to recover alkylamine. Alkylamine in the extractant phase is fractionally distilled to yield alkylamine and to recover the extractant solvent.

According to the second method for separating each component in the mother liquor, the mother liquor is acidified in the presence of an extractant solvent to dissolve long chain dibasic acid and alkanoic acid. After acidification and extraction, to the aqueous solution are added a basic agent and an extractant solvent to recover alkylamine. Long chain dibasic acid and alkanoic acid are separated from the extractant phase by cooling crystallization and distillation, respectively.

The third method for separating each component in the mother liquor starts with adding a basic agent and an extractant solvent to the solution to recover alkylamine, followed by adding an acid to the solution to form long chain dibasic acid and alkanoic acid in the presence or absence of an extractant solvent. In the absence of an extractant solvent, the long chain dibasic acid is precipitated and recovered by means of solid-liquid separation, and alkanoic acid is recovered as an oil phase in the mother liquor. In the presence of an extractant solvent, the long chain dibasic acid and alkanoic acid are dissolved in the extractant phase and separated by crystallization and distillation, respectively.

If there are long chain fatty acids present in the starting material, these fatty acids are precipitated as the ammonium salt, along with the long chain amino acid. In the production of 11-aminoundecanoic acid and dodecanedioic acid from the starting material of castor oil, significant amount of stearic acid is present in the mixed amide derivatives. Stearic acid is precipitated as the ammonium salt with 11-aminoundecanoic acid, because the ammonium salt of fatty acids is nearly insoluble in water.

The long chain amino acid is purified by dissolving the crude product in an aqueous acid solution in the presence of an organic extractant solvent. The separation of the long chain amino acid and fatty acids is thus accomplished by forming an aqueous solution of an acidic salt of the long chain amino acid and an organic extractant phase rich in fatty acids and impurities. It is particularly interesting to point out that colored materials are extracted into the extractant phase and the aqueous solution of the acid salt of long chain amino acid is nearly colorless.

Figure 2:
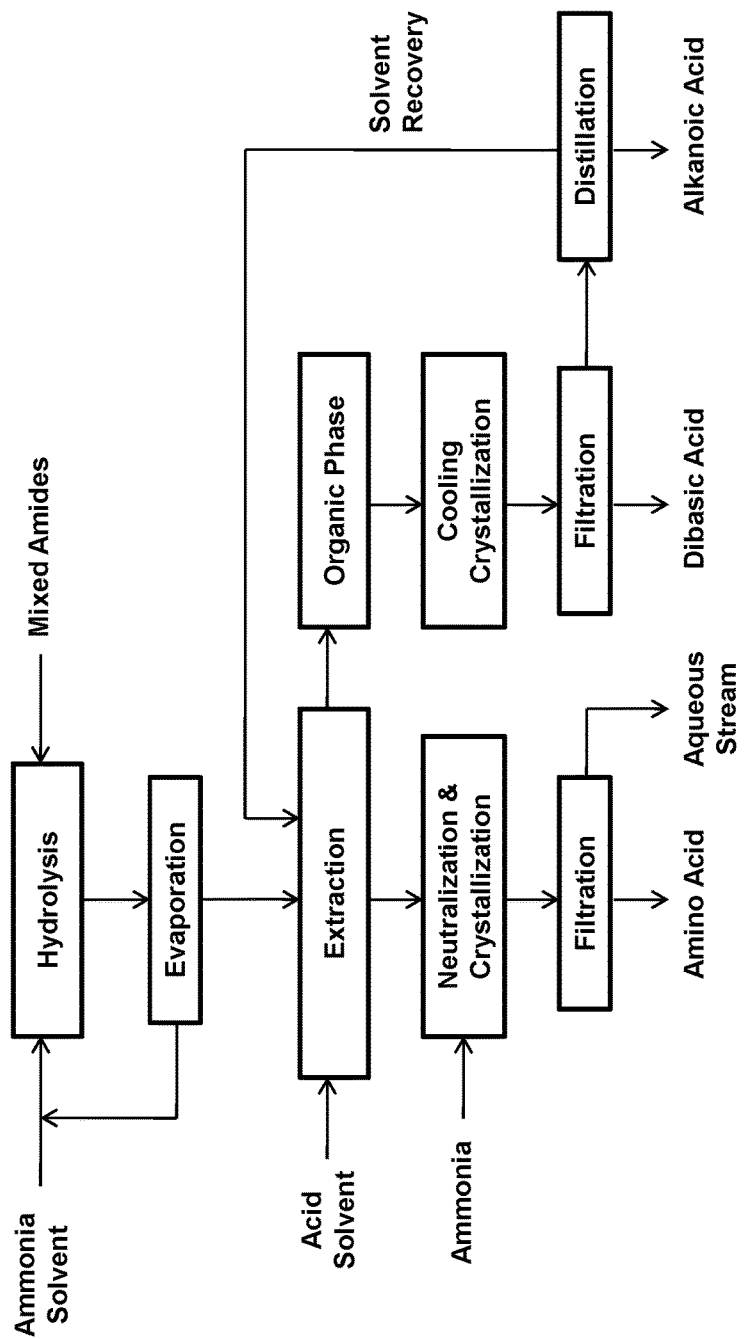
FIG. 2. Schematic flowchart for the production and separation of long chain amino acid, dibasic acid, alkylamine, and alkanoic acid from their mixture in the case of an ammonium hydroxide hydrolysis.

In another embodiment of the present invention, schematically illustrated in FIG. 2, the solution or suspension after removal of excess ammonia is acidified by adding an acid in the presence of an extractant solvent to form an aqueous solution of an acidic salt of the long chain amino acid and alkylamine and an organic extractant phase rich in long chain dibasic acid, alkanoic acid, fatty acids, and impurities. The long chain dibasic acid and alkanoic acid are separated by cooling crystallization and distillation of the extractant phase, respectively.

Suitable acids are an acid of a pKa<5.0. These acids are, but not limited to, inorganic acids, i.e., hydrochloric acid, hydrobromic acid, hydroiodic acid, sulfuric acid, nitric acid, phosphoric acid; alkyl and aryl sulfonic acids, i.e., methanesulfonic acid, ethanesulfonic acid, propanesulfonic acid, isethionic acid, benzenesulfonic acid, toluenesulfonic acid, xylenesulfonic acid, and sulfamic acid; organic carboxylic acids: malic acid, maleic acid, tartaric acid, glycolic acid, lactic acid, citric acid, oxalic acid, formic acid, acetic acid, and propionic acid. One or a mixture of two or more of these acids can be used to form an acidic salt of long chain amino acids.

Preferably, the acid is selected from one of the inorganic acids, and most preferably, sulfuric acid.

The aim of acidification is to completely convert the ammonium or alkylamine salts of long chain dibasic acids, short chain alkanoic acids, and fatty acids into free carboxylic acids and to form an acid salt of long chain amino acid, so as to ensure complete dissolution of long chain amino acid in aqueous phase and long chain dibasic acid in an organic extractant phase.

Organic solvents suitable for extracting dibasic acids, alkanoic acid, and fatty acids are water-insoluble and belong to the classes of ester, aliphatics, aromatics, ethers, alcohols of $C_4$ to $C_{10}$, and ketones of $C_4$ to $C_{10}$. Useful extractant solvents include, but not limited to, butyl formate, isobutyl formate, butyl acetate, isobutyl acetate, propyl acetate, isopropyl acetate, ethyl acetate, ethyl propionate, octyl acetate, benzene, toluene, xylene, cumene, anisole, diethyl ether, diisopropyl ether, dibutyl ether, methyl tert-butyl ether, ethyl tert-butyl ether, methyl tetrahydrofuran, petroleum ether, cyclohexane, dichloroethane, methylene chloride, chloroform, carbon tetrachloride, and trifluoromethylbenzene, n-butanol, isobutanol, amyl alcohol, isoamyl alcohol, hexanol, cyclohexanol, 2-ethylhexanol, isooctanol, sec-octanol, butanone, pentanone, hexanone, cyclohexanone, methyl isobutyl ketone. A single solvent or a mixture of two or more solvents can be used as extractant solvent.

Selected extractant solvent is expected to have good solubility of long chain dibasic acid and fatty acid at higher temperature, low or little solubility at lower temperature for the long chain dibasic acid and good solubility for fatty acid or the like at lower temperature to ensure an effective separation of long chain dibasic acid from other fatty acids rich in the organic phase.

Preferably, the extractant solvent is toluene.

The amount of extractant solvent is not limited, but is greater than the effective amount for the dissolution of dibasic acids and fatty acid impurities.

Temperature to perform acidification and extraction is in the range from 50° C. to the boiling point of the mixture of extractant organic phase rich in long chain dibasic acid and fatty acid and below 100° C. under normal pressure. Acidification and extraction can also be carried out at elevated temperature under pressure, but pressure equipment will be needed for the process.

Preferably, acidification and extraction are performed at a temperature from 60° C. to 95° C., and most preferably at a temperature from 80° C. to 90° C. At higher temperature, the higher solubility of long chain dibasic acid in the extractant solvent is advantageous in reducing the amount of the extractant solvent used.

There is no preference as to how an acid and an extractant solvent are introduced into the solution of ammonium or alkylamine salts of long chain dibasic acid and alkanoic acid. An acid and an extractant solvent can be added concomitantly, sequentially, continuously, semi-continuously, or batch wise.

In order to isolate long chain amino acid, the strongly acidic aqueous solution is neutralized with a basic agent to near neutral acidity in a pH range from 5 to 9. More preferably, the pH is in the range of 6 to 8. The neutralization is performed at a temperature from 50° C. to the boiling point of the solution, preferably from 60 to 90° C., most preferably from 70° C. to 80° C. Neutralization at this most preferred temperature produces larger crystals that will facilitate solid-liquid separation. After cooling to 0° C. to 30° C., preferably 15° C. to 25° C., the product, long chain amino acid, is precipitated and separated by means of solid-liquid separation, i.e., filtration or centrifuge, to yield a mother liquor containing inorganic salt and a small amount of long chain amino acid.

The basic agent is selected from the group consisting of ammonia, alkali and ammonium salts of hydroxide, bicarbonate, carbonate, sulfite, bisulfite, and carboxylate. A single agent or a mixture of two or more agents can be used. Preferably, the basic agent is ammonia or ammonium salts of hydroxide, bicarbonate, or carbonate.

The most preferable basic agent is ammonium hydroxide.

If ammonia or ammonium hydroxide is used as the basic agent to neutralize sulfuric acid, and after more basic agent is added to the mother liquor to a basic pH, alkylamine can only be recovered by extraction. Distillation of the basic solution will remove ammonia instead of alkylamine. It is interesting to note that alkylamine such as hexylamine is freely soluble in a solution of ammonium salt, i.e., ammonium sulfate, although hexylamine is insoluble in water or in a solution of alkali salt. No phase separation is observed between hexylamine and a solution of ammonium sulfate.

Figure 3:
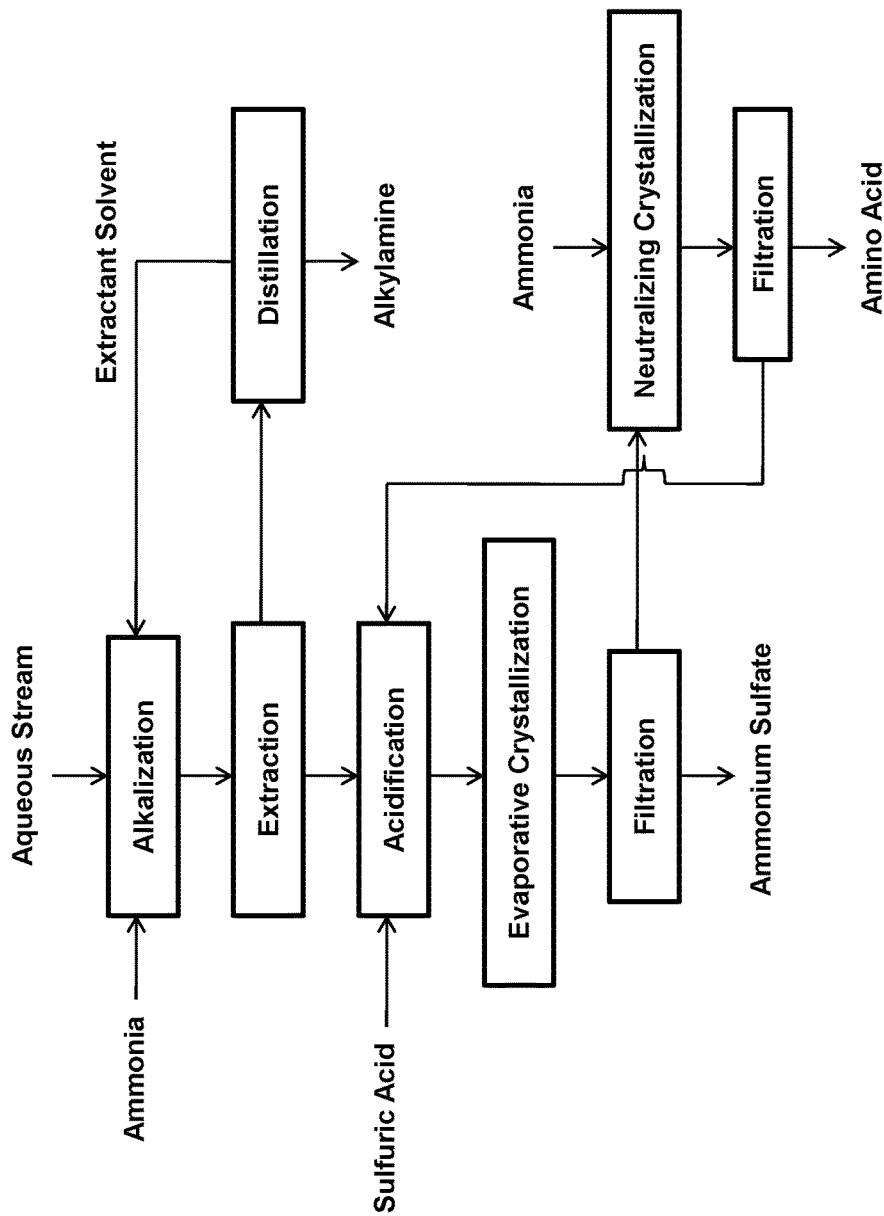
FIG. 3. Schematic flowchart for the treatment of aqueous streams to recover alkylamine, long chain amino acid, and ammonium sulfate.

The waste aqueous stream of the process according to the present invention contains alkylamine, a small amount of long chain amino acid, and ammonium sulfate when sulfuric acid is selected as the most preferable acid. The treatment of the aqueous solution is schematically illustrated in FIG. 3. The solution is acidified with sulfuric acid to increase the solubility of long chain amino acid and concentrated to precipitate ammonium sulfate. Neutralization of the concentrated solution with ammonia or ammonium hydroxide yields a precipitate of long chain amino acid, which is recovered by solid-liquid separation.

The process according to the present invention achieves the production and complete separation of long chain amino acids, dibasic acids, short chain alkanoic acid, alkylamine, and fatty acids without discharging any waste aqueous stream from the process. The only byproduct from the production process, ammonium sulfate, is a valuable commodity as a fertilizer.

EXAMPLES

The following examples illustrate the practice of this invention but are not intended to limit its scope.

Example 1

This example relates to the production and separation of 11-aminoundecanoic acid, dodecanedioic acid, hexylamine, heptanoic acid, and stearic acid from their mixture obtained from the ammonium hydroxide hydrolysis of the mixed amide derivatives.

A mixture of the products was obtained by hydrolyzing 150 g of the mixed amide derivatives prepared from methyl 12-ketostearate according to WO2017/088218 with 1200 mL of 10% ammonium hydroxide.

The mixed amide methyl esters was suspended in 1200 mL of 10% ammonium hydroxide in a 2 L autoclave and heated to 225° C. for 5 hours under a pressure of 65 bars. After cooling, the suspension was transferred to a 2 L flask and distilled with a 2.5×30 cm vacuum jacketed column packed with porcelain berl saddles to 101° C. to remove excess ammonia. The suspension became neutral at a pH in the range from 7 to 8 and cooled to room temperature. The precipitated 11-amminoundecanoic acid was recovered by filtration and washing with deionized water to provide a mother liquor. The crude product of brown color contained about 20% of ammonium stearate.

The crude product was dissolved in a mixture of 400 mL of 1 M sulfuric acid and 300 mL of toluene at 85° C. The mixture was vigorously stirred for 60 minutes at 85° C. and transferred to a separatory funnel to separate the aqueous phase. The dark-colored upper toluene phase was washed with hot deionized water and the washing was combined with the aqueous phase. After distilling off toluene, 14 g of stearic acid of yellow color was obtained.

To the colorless aqueous phase was added 1.0 g of activated carbon and stirred at 80° C. for 45 minutes and the solution was filtrated to obtain a clear, colorless solution. The solution was neutralized with a solution of ammonium hydroxide to a pH of 7.5 at about 70° C. to yield a crystalline suspension. After cooling to 25° C., the suspension was filtrated and the solid material washed three times with deionized water. After drying, 41.6 g of white 11-aminoundecanoic acid was obtained.

To the mother liquor of about 800 mL was added a solution of sulfuric acid to a pH 3.0 to precipitate dodecanedioic acid, which was recovered by filtration and washing with water, then methanol. After drying, 46.3 g of dodecanedioic acid was obtained.

The mother liquor was concentrated to 300 mL and an oil phase was separated to yield 24.5 g of heptanoic acid. To the solution was then added 50 mL of 25% ammonium hydroxide and extracted with 100 mL of toluene three times. The toluene phase was fractionally distilled to give 18.6 g of hexylamine.

The aqueous streams were combined and boiled to remove excess ammonia. Then 5 g of sulfuric acid was added to the solution. The solution was concentrated to precipitate ammonium sulfate, which was removed from the solution by filtration. To the solution of about 150 mL was added a solution of ammonium hydroxide to a pH of 7.5 to precipitate 0.6 g of 11-aminoundecanoic acid after filtration, washing with deionized water, and drying.

Example 2

This example relates to the production and separation of 11-aminoundecanoic acid, dodecanedioic acid, hexylamine, heptanoic acid, and stearic acid from their mixture obtained from the ammonium hydroxide hydrolysis of the mixed amide derivatives in 50% ethanol.

A mixture of the products was obtained by hydrolyzing 150 g of the mixed amide derivatives prepared from methyl 12-ketostearate according to WO2017/088218 with 1200 mL of 10% ammonium hydroxide containing 50% ethanol.

The mixed amide methyl esters were suspended in 1200 mL of 10% ammonium hydroxide containing 50% ethanol in a 2 L autoclave and heated to 225° C. for 5 hours. The suspension was transferred to a 2 L flask and distilled with a 2.5×30 cm vacuum jacketed column packed with porcelain berl saddles to 101° C. to remove excess ammonia and ethanol. The suspension became neutral at a pH of 7-8 and cooled to room temperature.

To the suspension were added 75 g of sulfuric acid and 800 mL of toluene. The mixture was vigorously stirred for 60 minutes at 85° C. and transferred to a separatory funnel to separate an aqueous phase and a toluene phase rich in dodecanedioic acid, heptanoic acid, and stearic acid.

The toluene phase was concentrated to 300 mL and cooled to 10° C. to crystallize dodecanedioic acid, which was separated by filtration. After drying, 28.4 g of dodecanedioic acid was obtained. The mother liquor to distilled to recover toluene and then under vacuum to yield 23.5 g of heptanoic acid. After distillation, the residual contains a mixture of 14 g of stearic and 12 g of dodecanedioic acid.

The aqueous phase was neutralized with a 25% solution of ammonium hydroxide to a pH at 7.5. After cooling to 25° C., the crystalline solid was filtered off, washed three times with deionized water, dried to yield 41.9 g of 11-aminoundecanoic acid. An additional 1.2 g of 11-aminoundecanoic acid was recovered from the mother liquor following the same procedure as described in Example 1.

To the mother liquor was added 50 mL of 25% ammonium hydroxide and extracted three times with 200 mL of toluene. The toluene phase was fractionally distilled to yield 21.8 g of hexylamine.

It will be understood that the foregoing examples, explanation, and drawings are for illustrative purpose only and that in view of the instant disclosure various modifications of the present invention will be self-evident to those skilled in the art and are to be included within the spirit and purview of this application and the scope of the claims.

What is claimed is:

1. A process for producing long chain amino acid, dibasic acid, short chain alkylamine, and alkanoic acid of the following structures:

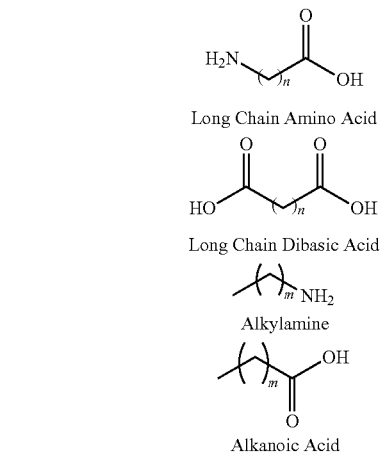

from an ammonia or ammonium hydroxide hydrolysis of the mixed amide derivatives of the following structures:

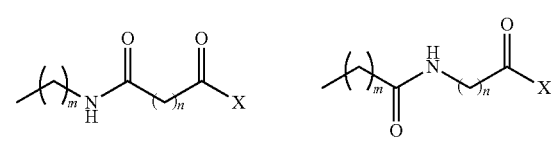

wherein m is an integer from 0 to 10;
n is an integer from 6 to 20;
X is OR or $NR_1R_2$, wherein OR is OH, $C_1$-$C_8$ monohydric alcohol, or $C_1$-$C_8$ polyhydric alcohol, and $R_1$ and $R_2$ are each independently hydrogen or $C_1$-$C_8$ alkyl group; comprising:
  (1) adding the mixed amide derivatives to an aqueous solution of ammonium hydroxide in the presence or absence of solvent or catalyst;
  (2) subjecting the solution or suspension of step (1) to an hydrolysis reaction; and
  (3) recovering excess ammonia and solvent in the presence of solvent in step (1) by evaporation to provide a mixture of long chain amino acid and alkylamine or ammonium salts of long chain dibasic acid and alkanoic acid.

2. The process according to claim 1, wherein the hydrolysis reaction is performed at a temperature from 100° C. to 280° C.

3. The process according to claim 1, wherein the hydrolysis reaction is performed at a temperature from 160° C. to 220° C.

4. The process according claim 1, wherein the hydrolysis reaction is performed under a pressure from autogenous to 260 bars.

5. The process according to claim 1, wherein the solvent is selected from the group consisting of methanol, ethanol, isopropanol, propanol, tetrahydrofuran, dioxane, tert-butanol, isobutanol, butanol, and a mixture of two or more thereof.

6. The process according to claim 1, wherein the catalyst is selected from the group consisting of alkali and ammonium salts of hydroxide, bicarbonate, carbonate, bisulfite, sulfite, sulfate, nitrate, phosphate, and a mixture of two or more thereof.

7. The process according to claim 1, wherein a process for separating long chain amino acid and ammonium or alkylamine salts of long chain dibasic acid and alkanoic acid comprises:
  (a) crystallizing long chain amino acid by cooling the mixture of hydrolysis solution or suspension;
  (b) separating the long chain amino acid by means of solid-liquid separation to provide a mother containing an ammonium or alkylamine salts of long chain dibasic acid and alkanoic acid;
  (c) adding an acid to the mother liquor of step (b) to precipitate the long chain dibasic acid and to form the alkanoic acid in the absence or presence of an extractant solvent;
  (d) separating the long chain dibasic acid by means of solid-liquid separation; and
  (e) recovering the alkanoic acid from the mother liquor or an extractant phase.

8. The process according to claim 1, wherein a process for separating long chain amino acid and ammonium or alkylamine salts of long chain dibasic acid and alkanoic acid comprises:
  (a) adding an acid and an extractant solvent to the the mixture of hydrolysis solution or suspension;
  (b) separating the aqueous phase of an acid salt of long chain amino acid and alkylamine and the extractant phase containing long chain dibasic acid, alkanoic acid, fatty acid, and impurities;
  (c) crystallizing long chain dibasic acid by cooling the extractant phase and separating the long chain dibasic acid by means of solid-liquid separation;
  (d) recovering the alkanoic acid from the mother liquor of step (c) by distillation;
  (e) neutralizing the aqueous solution of step (b) with a basic agent to neutral pH to precipitate the long chain amino acid; and
  (f) recovering the long chain amino acid of step (e) by means of solid-liquid separation.

9. The process according to claim 1, wherein a process for purifying long chain amino acid comprises:
  (a) dissolving the long chain amino acid in an acid aqueous solution in the presence of an extractant solvent;
  (b) separating the aqueous phase containing the acid salt of long chain amino acid and the extractant solvent phase rich in fatty acid and colored materials;
  (c) neutralizing the aqueous phase with a basic agent to precipitate the long chain amino acid; and
  (d) recovering the long chain amino acid by means of solid-liquid separation.

10. The process according to claim 1, wherein the acid is selected from the group consisting of hydrochloric acid, hydrobromic acid, hydroiodic acid, sulfuric acid, nitric acid, phosphoric acid, methanesulfonic acid, ethanesulfonic acid, propanesulfonic acid, isethionic acid, benzenesulfonic acid, toluenesulfonic acid, xylenesulfonic acid, sulfamic acid, malic acid, maleic acid, tartaric acid, glycolic acid, lactic acid, citric acid, oxalic acid, formic acid, acetic acid, propionic acid, and a mixture of two or more thereof.

11. The process according to claim 1, wherein the acid is sulfuric acid.

12. The process according to claim 1, wherein the extractant solvent is selected from the group consisting of butyl formate, isobutyl formate, butyl acetate, isobutyl acetate, propyl acetate, isopropyl acetate, ethyl acetate, ethyl propionate, octyl acetate, benzene, toluene, xylene, cumene, anisole, diethyl ether, diisopropyl ether, dibutyl ether, methyl tert-butyl ether, ethyl tert-butyl ether, methyl tetrahydrofuran, petroleum ether, cyclohexane, dichloroethane, methylene chloride, chloroform, carbon tetrachloride, and trifluoromethylbenzene, n-butanol, isobutanol, amyl alcohol, isoamyl alcohol, hexanol, cyclohexanol, 2-ethylhexanol, isooctanol, sec-octanol, butanone, pentanone, hexanone, cyclohexanone, methyl isobutyl ketone, and a mixture of two or more thereof.

13. The process according to claim 1, wherein the extractant solvent is toluene.

14. The process according to claim 1, wherein the basic agent is selected from the group consisting of ammonia, alkali and ammonium salts of hydroxide, bicarbonate, carbonate, bisulfite, sulfite, carboxylate, and a mixture of two or more thereof.

15. The process according to claim 1, wherein the basic agent is ammonia or ammonium hydroxide.

16. The process according to claim 1, wherein the long chain amino acids are 9-aminononanoic acid, 11-aminoundecanoic acid, or 13- aminotridecanoic acid.

17. The process according to claim 1, wherein the long chain amino acid is 11-aminoundecanoic acid.

18. The process according to claim 1, wherein the long chain dibasic acids are sebacic acid, dodecanedioic acid, or brassylic acid.

19. The process according to claim 1, wherein the long chain dibasic acid is dodecanedioic acid.

20. The process according to claim 1, wherein the short chain alkanoic acids are heptanoic acid and pelargonic acid.

21. The process according to claim 1, wherein the alkylamines are n-hexylamine and n-octylamine.

\* \* \* \* \*